(12) United States Patent
Grajcar (10) Patent No.: US 9,374,985 B2
(45) Date of Patent: Jun. 28, 2016

(54) METHOD OF MANUFACTURING OF A LIGHT EMITTING SYSTEM WITH ADJUSTABLE WATT EQUIVALENCE

(71) Applicant: ONCE Innovations, Inc., Plymouth, MN (US)

(72) Inventor: Zdenko Grajcar, Crystal, MN (US)

(73) Assignee: ONCE Innovations, Inc., Plymouth, MN (US)

( * ) Notice: Subject to any disclaimer, the term of this patent is extended or adjusted under 35 U.S.C. 154(b) by 0 days.

(21) Appl. No.: 13/715,884

(22) Filed: Dec. 14, 2012

(65) Prior Publication Data

US 2013/0157394 A1    Jun. 20, 2013

Related U.S. Application Data

(60) Provisional application No. 61/570,552, filed on Dec. 14, 2011.

(51) Int. Cl.
*H01L 33/58* (2010.01)
*A01K 61/00* (2006.01)
(Continued)

(52) U.S. Cl.
CPC .............. *A01K 61/00* (2013.01); *A01G 33/00* (2013.01); *A01K 61/005* (2013.01); *A01K 63/06* (2013.01); *C12M 21/02* (2013.01); *C12M 31/10* (2013.01); *C12N 1/12* (2013.01); *C12N 13/00* (2013.01); *F21K 9/135* (2013.01); *F21V 3/0418* (2013.01);
(Continued)

(58) Field of Classification Search
USPC ................ 257/88, 98, 99, E33.075, E33.058, 257/E33.061; 438/22, 26–28; 362/231, 234, 362/276, 294; 315/35, 309, 312
See application file for complete search history.

(56) References Cited

U.S. PATENT DOCUMENTS 3,939,802 A    2/1976    Neff
4,137,869 A    2/1979    Kipping
(Continued)

FOREIGN PATENT DOCUMENTS

CN    1042039 A    5/1990
CN    1692700 A    11/2005
(Continued)

OTHER PUBLICATIONS

Notification of Transmittal of the International Search Report and the Written Opinion of the International Searching Authority issued in International Patent Application No. PCT/US2012/069379 dated Feb. 25, 2013.
(Continued)

*Primary Examiner* — Marvin Payen
*Assistant Examiner* — Victor Barzykin
(74) *Attorney, Agent, or Firm* — McDermott Will & Emery LLP (57) ABSTRACT

A method of manufacturing multiple light emitting diode lighting assemblies each having a different initial light output is provided. A first heat sink is manufactured and a first platform assembly with a plurality of light emitting diodes is formed with an automated device. The automated device selects a first predetermined lumen output. A second heat sink is then manufactured using the same manufacturing process, and a second platform assembly with a plurality of light emitting diodes is formed with the automated device. During this time, the automated device selects a second predetermined lumen output based on information inputted into the automated device.

7 Claims, 10 Drawing Sheets

(51) Int. Cl.

| | | |
|---|---|---|
| *F21V 31/00* | (2006.01) | |
| *A01G 33/00* | (2006.01) | |
| *H01L 33/64* | (2010.01) | |
| *A01K 63/06* | (2006.01) | |
| *C12N 1/12* | (2006.01) | |
| *C12N 13/00* | (2006.01) | |
| *F21V 3/04* | (2006.01) | |
| *C12M 1/00* | (2006.01) | |
| *F21V 29/58* | (2015.01) | |
| *F21K 99/00* | (2016.01) | |
| *F21S 2/00* | (2016.01) | |
| *F21V 23/04* | (2006.01) | |
| *F21Y 101/02* | (2006.01) | |
| *F21Y 103/00* | (2016.01) | |

(52) U.S. Cl.
CPC ............... *F21V 3/0472* (2013.01); *F21V 29/58* (2015.01); *F21V 31/00* (2013.01); *H01L 33/58* (2013.01); *H01L 33/64* (2013.01); *F21S 2/00* (2013.01); *F21V 23/04* (2013.01); *F21V 23/0442* (2013.01); *F21Y 2101/02* (2013.01); *F21Y 2103/003* (2013.01); *H01L 2224/48091* (2013.01); *H01L 2924/13091* (2013.01)

(56) References Cited

U.S. PATENT DOCUMENTS

| | | | |
|---|---|---|---|
| 4,379,437 A | 4/1983 | Knowles | |
| 4,699,086 A | 10/1987 | Mori | |
| 4,699,087 A | 10/1987 | Mori | |
| 4,703,719 A | 11/1987 | Mori | |
| 5,161,481 A | 11/1992 | Laufer | |
| 5,495,147 A | 2/1996 | Lanzisera | |
| 5,602,709 A | 2/1997 | Al-Dabbagh | |
| 5,713,303 A | 2/1998 | Willinsky et al. | |
| 5,850,806 A | 12/1998 | Mark et al. | |
| 5,937,791 A | 8/1999 | Baugher et al. | |
| 6,166,496 A | 12/2000 | Lys et al. | |
| 6,347,908 B1 | 2/2002 | Safwat | |
| 6,361,192 B1* | 3/2002 | Fussell et al. | 362/331 |
| 6,421,952 B1 | 7/2002 | Vascocu | |
| 6,636,003 B2 | 10/2003 | Rahm et al. | |
| 6,933,707 B2 | 8/2005 | Allen | |
| 7,038,399 B2 | 5/2006 | Lys et al. | |
| 7,081,722 B1 | 7/2006 | Huynh et al. | |
| 7,102,334 B2 | 9/2006 | Wiegand et al. | |
| 7,102,344 B1 | 9/2006 | Short | |
| 7,213,942 B2 | 5/2007 | Jiang et al. | |
| 7,220,018 B2 | 5/2007 | Crabb et al. | |
| 7,288,902 B1 | 10/2007 | Melanson | |
| 7,352,138 B2 | 4/2008 | Lys et al. | |
| 7,358,679 B2 | 4/2008 | Lys et al. | |
| 7,378,805 B2 | 5/2008 | Oh et al. | |
| 7,391,630 B2 | 6/2008 | Acatrinei | |
| 7,425,801 B2 | 9/2008 | Ozaki | |
| 7,489,086 B2 | 2/2009 | Miskin et al. | |
| 7,709,774 B2 | 5/2010 | Schulz et al. | |
| 7,737,643 B2 | 6/2010 | Lys | |
| 7,781,979 B2 | 8/2010 | Lys | |
| 7,791,289 B2 | 9/2010 | Oosterbaan et al. | |
| 7,847,486 B2 | 12/2010 | Ng | |
| 7,859,196 B2 | 12/2010 | Lee et al. | |
| 7,863,831 B2 | 1/2011 | Vos | |
| D632,837 S | 2/2011 | Grajcar | |
| 7,880,400 B2 | 2/2011 | Zhou et al. | |
| 7,902,769 B2 | 3/2011 | Shteynberg et al. | |
| 7,936,135 B2 | 5/2011 | Hum et al. | |
| D641,520 S | 7/2011 | Grajcar | |
| 7,977,892 B2 | 7/2011 | Lee et al. | |
| 8,102,167 B2 | 1/2012 | Irissou et al. | |
| 8,120,279 B2 | 2/2012 | Oosterbaan et al. | |
| 8,134,303 B2 | 3/2012 | Lys | |
| 8,159,125 B2 | 4/2012 | Miao | |
| 8,164,276 B2 | 4/2012 | Kuwabara | |
| 8,188,679 B2 | 5/2012 | Hoogzaad | |
| 8,188,687 B2 | 5/2012 | Lee et al. | |
| 8,324,642 B2 | 12/2012 | Grajcar | |
| 8,324,840 B2 | 12/2012 | Shteynberg et al. | |
| 8,373,363 B2 | 2/2013 | Grajcar | |
| 8,384,307 B2 | 2/2013 | Grajcar | |
| 8,531,136 B2 | 9/2013 | Grajcar | |
| 8,593,044 B2 | 11/2013 | Grajcar | |
| 8,598,799 B2 | 12/2013 | Tai et al. | |
| 8,643,308 B2 | 2/2014 | Grajcar | |
| 8,796,955 B2 | 8/2014 | Grajcar | |
| 8,922,136 B2 | 12/2014 | Grajcar | |
| 2002/0047606 A1 | 4/2002 | Guthrie et al. | |
| 2002/0097007 A1 | 7/2002 | Koncz et al. | |
| 2002/0149929 A1 | 10/2002 | Evans et al. | |
| 2003/0222503 A1* | 12/2003 | Lam et al. | 307/38 |
| 2005/0128751 A1 | 6/2005 | Roberge et al. | |
| 2005/0212458 A1 | 9/2005 | Powers, Jr. et al. | |
| 2005/0236998 A1* | 10/2005 | Mueller et al. | 315/51 |
| 2005/0280964 A1 | 12/2005 | Richmond et al. | |
| 2006/0214603 A1 | 9/2006 | Oh et al. | |
| 2007/0069663 A1 | 3/2007 | Burdalski et al. | |
| 2007/0176182 A1 | 8/2007 | Wen et al. | |
| 2007/0182338 A1 | 8/2007 | Shteynberg et al. | |
| 2007/0258240 A1 | 11/2007 | Ducharme et al. | |
| 2007/0268702 A1 | 11/2007 | McFadden | |
| 2008/0203936 A1 | 8/2008 | Mariyama et al. | |
| 2008/0211421 A1 | 9/2008 | Lee et al. | |
| 2008/0273331 A1 | 11/2008 | Moss et al. | |
| 2009/0080187 A1* | 3/2009 | Chou | 362/231 |
| 2009/0160370 A1 | 6/2009 | Tai et al. | |
| 2009/0267534 A1 | 10/2009 | Godbole et al. | |
| 2010/0013402 A1 | 1/2010 | Chaffai et al. | |
| 2010/0060175 A1 | 3/2010 | Lethellier | |
| 2010/0164579 A1 | 7/2010 | Acatrinei | |
| 2010/0165677 A1 | 7/2010 | Wang et al. | |
| 2010/0237800 A1 | 9/2010 | Kang et al. | |
| 2010/0239441 A1 | 9/2010 | Bade et al. | |
| 2010/0268390 A1 | 10/2010 | Anderson | |
| 2010/0308739 A1 | 12/2010 | Shteynberg et al. | |
| 2010/0308751 A1 | 12/2010 | Nerone | |
| 2011/0012157 A1 | 1/2011 | Shi | |
| 2011/0031890 A1 | 2/2011 | Stack | |
| 2011/0037415 A1 | 2/2011 | Juestel et al. | |
| 2011/0084619 A1 | 4/2011 | Gray et al. | |
| 2011/0089830 A1* | 4/2011 | Pickard et al. | 315/32 |
| 2011/0101410 A1 | 5/2011 | Lin et al. | |
| 2011/0101883 A1 | 5/2011 | Grajcar | |
| 2011/0273103 A1 | 11/2011 | Hong | |
| 2011/0279015 A1* | 11/2011 | Negley et al. | 313/501 |
| 2011/0291135 A1* | 12/2011 | Hsieh et al. | 257/98 |
| 2011/0316420 A1 | 12/2011 | Chang | |
| 2012/0013238 A1* | 1/2012 | Jonsson | 313/110 |
| 2012/0081009 A1 | 4/2012 | Shteynberg et al. | |
| 2012/0098458 A1 | 4/2012 | Dai et al. | |
| 2012/0212129 A9* | 8/2012 | Chou et al. | 315/35 |
| 2012/0268918 A1 | 10/2012 | Grajcar | |
| 2013/0027947 A1* | 1/2013 | Villard et al. | 362/294 |
| 2013/0058103 A1* | 3/2013 | Jiang et al. | 362/296.05 |
| 2013/0134888 A1 | 5/2013 | Grajcar | |
| 2013/0153938 A1 | 6/2013 | Grajcar | |
| 2013/0187572 A1 | 7/2013 | Grajcar | |
| 2013/0193864 A1 | 8/2013 | Angeles | |
| 2014/0197741 A1 | 7/2014 | Sakai et al. | |

FOREIGN PATENT DOCUMENTS

| | | |
|---|---|---|
| CN | 101162847 | 4/2008 |
| CN | 201344401 Y | 11/2009 |
| CN | 101868529 A | 10/2010 |
| EP | 1502483 | 2/2005 |
| EP | 1610593 A2 * | 12/2005 |
| EP | 2094063 | 8/2009 |
| JP | 2004248333 | 9/2004 |
| JP | 2006147933 | 6/2006 |
| JP | 2006244848 | 9/2006 |
| JP | 2007511903 | 5/2007 |
| JP | 2007299788 | 11/2007 |

(56) References Cited

FOREIGN PATENT DOCUMENTS

| | | |
|---|---|---|
| JP | 2008218043 | 9/2008 |
| JP | 4241870 | 3/2009 |
| JP | 2009117036 | 5/2009 |
| JP | 2009123427 | 6/2009 |
| JP | 2011004071 | 1/2011 |
| JP | 4796027 | 10/2011 |
| JP | 5676611 | 1/2015 |
| WO | 2001006630 | 1/2001 |
| WO | 2005084080 | 9/2005 |
| WO | 2009/066231 A2 | 5/2009 |
| WO | 2011/019288 A2 | 2/2011 |

OTHER PUBLICATIONS

Notification of Transmittal of the International Search Report and the Written Opinion of the International Searching Authority issued in International Patent Application No. PCT/US12/68701 dated Dec. 10, 2012.
International Preliminary Report on patentability issued in International Application No. PCT/US20121068701 dated Jun. 26, 2014.
International Preliminary Report on patentability issued in International Application No. PCT/US2012/069728 dated Jun. 17, 2014.
International Preliminary Report on patentability issued in International Application No. PCT/US2012/069379 dated Jun. 17, 2014.
Office Action dated Aug. 14, 2014 issued in U.S. Appl. No. 13/585,806.
U.S. Office Action dated Nov. 21, 2014 issued in corresponding U.S. Appl. No. 13/715,904.
US Office Action issued in U.S. Appl. No. 13/585,806 dated Mar. 6, 2015.
"Hazards of Harmonics and Neutral Overloads", White Paper #26, 2003, pp. 1-8, American Power Conversion.
"Great Green Hope: The Corporate Love Affair with Algae", Todd Taylor, Biomass Magazine, Apr. 2010 issue.
International Preliminary Report on Patentability, issue in International Patent Application No. PCT/US2010/045467, dated Feb. 14, 2012.
International Search Report and Written Opinion, issued in International Patent Application No. PCT/US2010/045467, dated Oct. 7, 2010.
International Preliminary Report on Patentability, issued in International Patent Application No. PCT/US2010/054506, dated May 1, 2012.
International Search Report and Written Opinion issued in International Patent Application No. PCT/US2010/054506, dated Dec. 28, 2010.
English translation of JP office action dated Mar. 4, 2014 for JP application No. 2012-524899.
English translation of CN office action dated Jan. 24, 2014 for CN application No. 2010800468806.
English translation of JP office action dated Apr. 1, 2014 for JP application No. 2012-524901.
English translation of CN office action dated Feb. 10, 2014 for CN application No. 201080046791.1.
English translation of second CN office action dated Sep. 3, 2014 for CN application No. 201080046791.1.
International Preliminary Report on Patentability and Written Opinion of the International Searching Authority issued in International Patent Application No. PCT/US2012/022059, dated Mar. 25, 2014.
U.S. Office Action dated Jan. 23, 2014 issued in U.S. Appl. No. 13/585,806.
Hongshan Su: "Fish Culture in Light Net Pen Underwater" (title also translated as "Test of Fish Farming in Underwater Lighting Cage"), Journal of Zoology, vol. 2,1983, pp. 31-32, with English translation.
Office Action issued in Chinese Application No. 201280070124.6, dated May 18, 2015, with English translation.
U.S. Office Action issued in U.S. Appl. No. 13/585,806 dated Sep. 11, 2015.
U.S. Office Action issued in U.S. Appl. No. 13/715,904 dated Aug. 14, 2015.

* cited by examiner

METHOD OF MANUFACTURING OF A LIGHT EMITTING SYSTEM WITH ADJUSTABLE WATT EQUIVALENCE

CROSS REFERENCE

This application claims benefit to and is based upon U.S. Provisional Patent Application Ser. No. 61/570,552 filed Dec. 14, 2011 entitled LED Lighting Structures and that application is incorporated by reference in full.

BACKGROUND OF THE INVENTION

This invention relates to a light emitting diode (LED) lighting assembly. More specifically, this invention relates to an LED lighting assembly that minimizes the components of the lighting structure.

LED lighting systems have begun to be used to replace the typical incandescent light bulb. Because LED lighting systems use LEDs as their source of light instead of a filament, the need for a vacuum chamber is eliminated and power requirements are greatly reduced. Further, as a result the need of heat sinks for the circuitry of LED lighting assemblies that comprise a majority of the size of the LED lighting assemblies LED lighting assemblies do not have the same characteristics as the typical incandescent light bulb.

As a result of these differences a new manner of classifying light bulbs had to be developed. In particular, as LED lighting assemblies were being advertised and promoted companies would attempt to compare their product to known incandescent light bulbs in the field. This lead to many false claims and comparisons confusing consumers. As a result the Environmental Protection Agency (EPA) has developed standards and labeling requirements to protect the consumer and allow all manufacturers and sellers of different lights to know how different lights are classified. These standards are known as Energy Star® requirements as indicated in the document entitled Energy Star® Program Requirements for Integral LED Lamps Eligibility Criteria—Version 1.4.

As an example, for omnidirectional lamp types (lamp types A, BT, P, PS, S, T (per ANSI C79.1-2002)) multiple criteria have been determined including minimum Luminous Efficacy, LED lamp power<10 W, LED lamp power>10 W, Minimum Light Output, Luminous Intensity Distribution, Maximum lamp diameter, Maximum overall length, Lumen Maintenance and Rapid-Cycle Stress Test. To illustrate, for omnidirectional lamp types for the Minimum Light Output the "Lamp shall have minimum light output (initial total luminous flux) at least corresponding to the target wattage of the lamp to be replaced" where target wattages between the given levels may be interpolated. Thus, for an LED lamp to be considered an equivalent of 40 watt incandescent light bulb the minimum initial light output of the LED lamp must be 450 lumens, for an equivalent 60 watt incandescent light bulb a minimum of 800 lumens must be shown and for an equivalent to a 75 watt incandescent light bulb 1,100 lumens must be shown.

Thus a need in the art exists to present a LED lighting assembly and manufacturing process that presents a simple process for manufacturing LED lighting assemblies meeting criteria of any lamp type. Further there is a need to provide an efficient manufacturing process in order to mass produce different lamp types using a single LED lighting module.

Typical LED lighting devices are complex and therefore expensive and difficult to manufacture. This is a result of complex circuitry used to power the LEDs that with the LEDs generates excessive amounts of heat. Thus in existing LED lighting devices, the heat transfer pathway is complex because heat transfer is required for both the LEDs and the LED driving circuitry. An aluminum heat sink generally handles heat dissipation for multiple heat sources such as from the LED holding mechanism and the AC power circuitry. The aluminum is expensive driving the cost to manufacture upwards.

The heat from the different heat sources needs to be moved or channeled to the heat sink. Generally, a heat sink moves the heat away from the electronic components to dissipate the heat. In some devices, around 40% to 60% of the energy going into an LED is dissipated (or wasted) as heat. The driver/power circuitry may be around 80% efficient. In current systems, there are several different locations from which the thermal sources (LED and circuitry) create the heat. Therefore the heat sink included in a LED light is complex.

In addition, the electronics in existing LED lighting devices are large and generally are mounted on a separate structure (e.g., an assembly or substrate) from the structure supporting the LEDs. In existing LED lighting devices, these functions are accomplished through a variety of different sub components where the LEDs are carried on one module, the driver circuitry (regardless of size) is carried on a separate discrete module, the heat sink function is accomplished through several conductive processes. Thus, preexisting devices include multiple discrete components that each separately keep the LEDs, power conditioning, mechanical support (structure) and heat transfer functionalities distinct and separate.

Other devices use additional or distinct mechanical structures or constructs to carry or hold the conditioning circuitry, the heat transfer and the LED elements. Such devices, for example, may include a support onto which the various components (e.g., conditioning circuitry, heat transfer/sink, LEDs, etc) are mounted. In addition, in existing lighting devices, the discrete modules including in the devices are connected to each other using standard wires, connections and/or solder (on the PCB of some designs). Further, the system for diffusion of the light which can be incorporated within a LED lighting device is difficult and inefficient to produce.

Another problem with current LED lighting devices is the cost of components and inventory management of bulbs having different wattage ratings is high. Currently, every light bulb is unique—a 60 W bulb differs from a 100 W in the manufacture of the key components and assembly of the bulb. As a result, such lights bulbs having different wattage ratings cannot necessarily be produced on a same production line. Likewise, creating different bulbs require multiple inventory factors. As a result, separate inventories of light bulbs of each wattage rating may be needed, resulting in large light bulb inventories.

Another problem exists in current designs where electronics are positioned within or along a heat sink. The electronics also create heat that diffuses in all directions, including back towards the LED substrate/heat spreader. Thus, in existing designs, the LEDs and circuitry are located on different substrates, and the heat produced by the LEDs and circuitry in these designs therefore have different thermal pathways that can work against each other. These designs may need to have multiple thermal pathways for their process, for example in designs that do not place heat-producing driving circuitry (regardless of the circuitry's complexity) and LEDs in a manner such that their vectors of thermal conduction move in different directions.

A further problem with current LED light assemblies is that in order to be configured to be compatible with standard incandescent light-bulbs and light sockets/figures (such as the Edison A19 bulb, as well as other bulbs), the power must be moved by wires to move and return the current from the base to the electronics. Alternatively, the power collected and returned to the socket is completed through the standard base unit, the screw-in portion of a screw-in bulb. These design approaches increase costs and manufacturing complexity (connecting wires to both ends and snaking wires up through some cavity from the base to the electronics).

Thus a principle object of the present invention is to reduce the number of parts in a typical LED lighting device.

Yet another object of the present invention is to reduce manufacturing cost associated with making LED lighting devices.

These and other objects, features and advantages will become apparent from the specification and claims.

BRIEF SUMMARY OF THE INVENTION

A light emitting diode assembly having a heat sink and a platform assembly secured to the heat sink. The platform assembly has a substrate with a plurality of light emitting diode elements disposed thereon and in electric communication with an AC input to produce an initial light output. Where a first predetermined lumen output or a second predetermined lumen output can be provided by the platform assembly using the same manufacturing method. In this manner assemblies can be made from the same manufacturing process having different equivalent wattages.

DETAILED DESCRIPTION OF A PREFERRED EMBODIMENT OF THE INVENTION

The figures show a light emitting diode (LED) lighting assembly 10. The LED lighting assembly 10 includes a base 12 that has electrical conducting elements 14 such that the base 12 can be inserted into a traditional lighting socket to receive an AC power input. The base 12 is threadably secured to a heat sink 16. In one embodiment the heat sink 16 is made of fly ash. In particular fly ash is inexpensive in cost and lower weight. While not as an effective heat sink 16 as other more expensive materials, a lower quality heat sink 16 can be used. Still, the heat sink design using fly-ash needs to factor in the worst-case tolerance for a lot of low quality fly ash materials, to ensure that the heat sink performance always meets the minimum required performance.

The heat sink 16 has a body 18 that extends from a first end 20 to a second end 22. At the first end 20 is a connecting body 23 that can be of one piece construction and part of the heat sink 16 or optionally a separate body secured to the heat sink 16. The connecting body has threads 24 that threadably receive the base 12. A centrally located conduit 26 extends from adjacent the first end 20 of the body 18 to the second end 22 of the body 18. The conduit 26 receives a conductive element 28 or wiring that extends through the body 18 and provides an electrical communication path from a socket via the base 12 through the heat sink 16.

A heat sink base 30 is part of the connecting body 23 and is located adjacent the threads 24 at the first end 20 of the heat sink 16. In one embodiment the heat sink base 30 is a round surface having a plurality of openings 32 for receiving a plurality of primary fin members 34 that extend radially from adjacent the conduit 26. The plurality of primary fin members 34 are attached and secured within the openings 32 and extend upwardly away from the heat sink base 30 and radially away from the conduit 26 to form an arcuate outer surface 36 that extends to a point 38 of a pointed section 40 where the pointed section 40 extends from a flange 42 that is secured to the underside of a platform base 44. The platform base 44 in one embodiment is round with a single outer edge 45 and has a square shaped indention 46 disposed therein surrounding an opening 48 that aligns with the terminating end of the conduit 26 to provide a path for the conductive element 28. The outer edge 45 is spaced apart from the pointed section 40 to form a notch 49 on the flange 42 between the outer edge 45 and pointed section 40.

A plurality of support members 50 similar to the primary fin members 34 are attached and secured within the openings 32 and extend away from the heat sink base 30 and radially away from the conduit to form an arcuate outer surface 52 that terminates at an end 54 that engages and extends along the bottom surface of the platform base 44. In one embodiment the end 54 is secured to the platform base 44 such that a lip 56 extends past the platform base. Each support member 50 is positioned between consecutive primary fin members 34 where in one embodiment the support member 50 is equidistance from the primary fin members 34.

A plurality of secondary fin members 58 are secured to the bottom surface of the platform base 44 and extend downwardly away from the platform base 44. While most of the secondary fin members 58 are secured to the bottom of the platform base 44 adjacent the edge 45 of the platform base 44, a few selected secondary fin members 58 are offset from the edge 45 to form an engagement surface 59 on the bottom of the platform base 44. The secondary fin members 58 are also located between primary fin members 34 and support members 58.

In embodiments utilizing a heat sink 16 a thermally and electrically conductive adhesive is provided to move thermal vectors in the same direction. Specifically, heat does not dissipate well up into a first quadrant above the platform base 44 of the lighting assembly 10. Therefore, a design directing vectors of thermal conduction in the same direction downwardly into at second quadrant within the platform base 44. In particular, a combined and unified vector of thermal conduction has a direction that points away from the platform base 44 toward the second quadrant and has a magnitude that is reduced as it proceeds through the heat sink 16.

As shown in FIGS. 4-7 a platform assembly 60 is provided where each of the primary fin members 34, support members 50 and secondary fin members 58 have ridges that convey or transfer heat away from a platform assembly 60 mounted on the platform base 44. The platform assembly 60 is mounted in the indentation 46 of the platform base 44 and has a common processing engine 62. In one embodiment the common processing engine 62 includes electrical component dies 64 that receive electricity from an AC input 66. The AC input 66 receives alternating current (AC) from the electrical conducting elements 14 that include protection elements 70 such as a fuse 72 and MOV 74 that in one embodiment are shrink or heat wrapped to the electrical conducting elements. Thus a rectifier 68 receives electricity from the AC input 66 that is protected.

Figure 5:
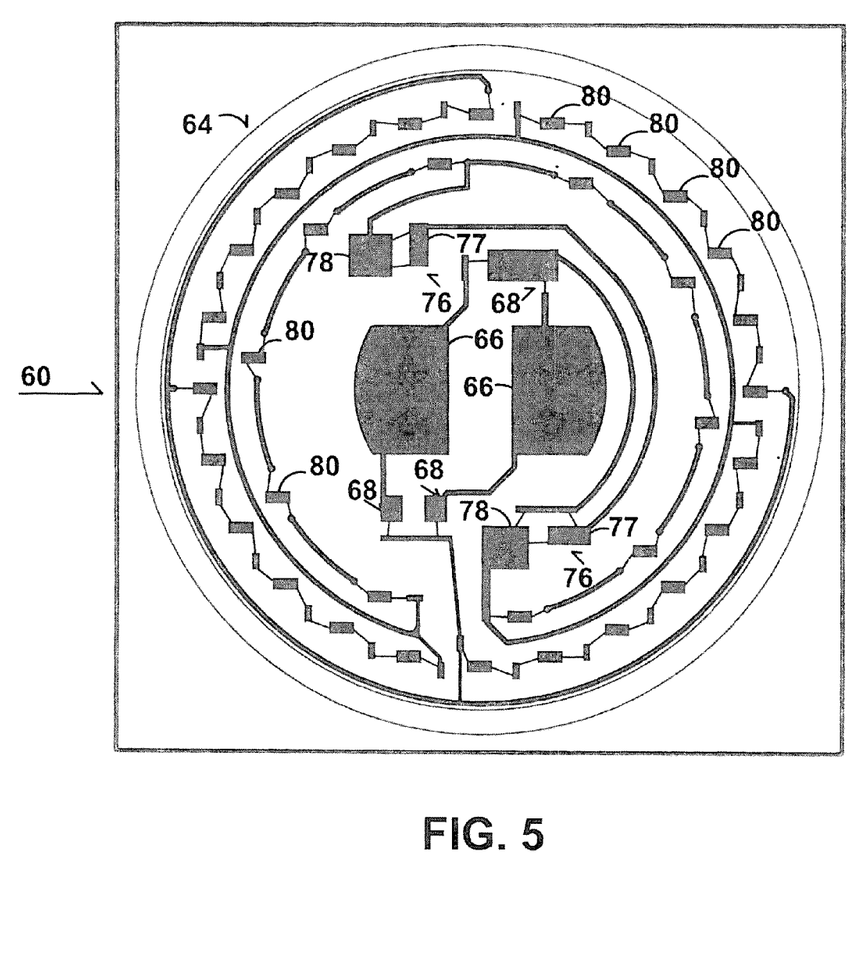
FIG. 5 is a top plan view of an engine of a platform assembly of a light emitting assembly.
Figure 6:
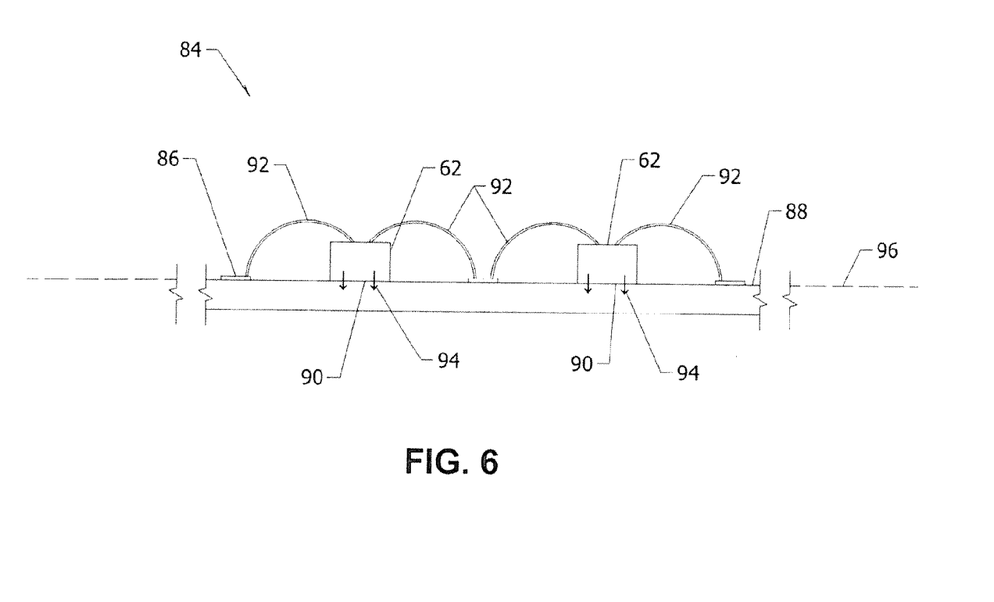
FIG. 6 is a cut away side plan view of the substrate of a light emitting assembly.

Driving elements 76 that in one embodiment are dies comprise the engine 62. The driving elements 76 include at least one resistor 77, transistors 78 such as MOSFETs, IGFETs, or the like for powering and dimming a plurality of light emitting diode (LED) elements 80 that in one embodiment are LED dies. The platform assembly 60 is electrically connected to the electrical conducting elements 14 such that the driving elements 76 power the LED elements 80.

Based on this design as the current is increased, or the system is driven harder to increase lumen output from the LED dies 80, because of the simplicity of the design the heat is able to flow directly through the substrate to the thermal interface to the heat sink 16. In this manner the platform assembly 60 has a selectable brightness or wattage rating. Specifically the amount of lumens of the initial light output as indicated in the Energy Star® requirements as indicated in the document entitled Energy Star® Program for Integral LED Lamps Eligibility Criteria—Version 1.4 of the platform assembly 60 can thus be provided by the platform assembly 60.

In particular, as an example in one embodiment, in a first mode when the total resistance of the resistor or resistors 77 is at a first predetermined level the LED platform 60 is able to selectively operate within a first predetermined lumen range or at a first predetermined equivalent wattage. In one embodiment the first predetermined lumen range is between 450 and 800 lumen. In another embodiment the first predetermined lumen range is between 800 and 1100 lumens. In yet another embodiment the first predetermined lumen range is between 1100 and 1600 lumens. In still another embodiment the first predetermined lumen range has outputs greater than 1600 lumens.

Similarly, in a second mode when the total resistance of the resistor or resistors 77 is at a second predetermined level the LED platform 60 is able to selectively operate with a second predetermined lumen range or at a second predetermined equivalent wattage. In one embodiment the second predetermined lumen range is between 450 and 800 lumen. In another embodiment the second predetermined lumen range is between 800 and 1100 lumens. In yet another embodiment the second predetermined lumen range is between 1100 and 1600 lumens. In still another embodiment the second predetermined lumen range has outputs greater than 1600 lumens.

Thus, the LED platform 60 is able to selectively operate with different predetermined lumen ranges from a single manufacturing process. Further, if needed, differing heat sinks can be provided that further spread heat through the sink 16 from the platform 60. For example, heat sinks as shown in U.S. provisional application No. 61/707,313 entitled Modular LED Lighting Assembly Utilizing Structures of a Dwelling as a Heat Sink by Grajcar that is incorporated in full herein.

Therefore, during the manufacturing process when the platform assembly is being manufactured by an automated machine one need only program into the machine the amount or type of resistor 77 or how hard or the milli amps required for the platform is to be driven to control or determine the lumen range of the initial light output. Thus, when different lumen ranges are required an entire new line or different lighting assembly does not need to be created with different parts or components. Instead information can be quickly inputted into a machine and a new lighting product is instantly created.

The processing engine 62 in one embodiment is formed on a substrate 84 that in one embodiment is a printed circuit board. Alternatively the substrate 84 is a hybrid substrate, or takes the form of other types of electric circuits. The substrate 84 can be any shape or size and in one embodiment is circular in shape and the LED dies 80 are arranged in series in any pattern, including arcuately around the circular substrate. Further the transistors 78 and LED dies 80 can be arranged to present a bypass circuit that allows dimming and additional control of the LED dies 80.

The substrate 84 of the improved LED lighting platform can also orient the LED dies 80 to project the light in one or more selected direction(s), without requiring any additional element or secondary carrier or structure upon which the LED dies 80 are placed in order to direct the light. In one example, a single planar element allows for manufacturing using standard electronics manufacturing, and for directing light in a direction away from the plane of the substrate 84 or mechanical support.

Although the above configuration using a single planar element or substrate 84 provides for simpler manufacturing, the substrate 84 or mechanical support need not have a planar configuration, but may instead have any number of shapes. In one example, the mechanical support may be a cube, allowing LED dies 80 to be placed on all six sides, for example, or a sphere with LED dies 80 distributed on the sphere's surface.

In another example, the LED dies 80 may be placed on any number of substructures formed on the single plane (or surface) of the mechanical carrier/support 44. In the example, the single plane (or surface) may have ridges or pyramids built up from the plane, and the LED dies 80 are placed on the ridges or pyramids in order for the light produced by the LED dies 80 to be directed at angles which are not necessarily orthogonal to the plane.

The substrate 84 additionally functions as a heat-conducting or spreading substrate that is formed of a heat conducting material, such as a ceramic material, a material used for hybrids, or the like. Alternatively the materials for this substrate 84 may be any number of technologies, including a simple printed circuit board, or heat conductive plastics with conductive polymers.

The electrical component dies 64 can be securely mounted directly on the heat-diffusing substrate 84 using an adhesive or other attachment method that conducts heat from the engine 62 and LED dies 80 to the heat-diffusing substrate 84. Thus, the elements (i.e., engine 62 and LED dies 80) can be bonded to the substrate 84 through thermally and electrically conductive material. In this embodiment the heat conduction is accomplished through the thermally conductive epoxy that connects electrical elements to the electrically active substrate 84.

In another embodiment, the electrical component dies 64 are placed onto the substrate 84 are bonded to the electrically active hybrid/substrate 84 through wire bonds. In yet another embodiment the LED lighting platform 60 can also include several of the components within the substrate 84, for example, by forming a resistor directly into the substrate 84 as a resistive electrical pathway.

Figure 7:
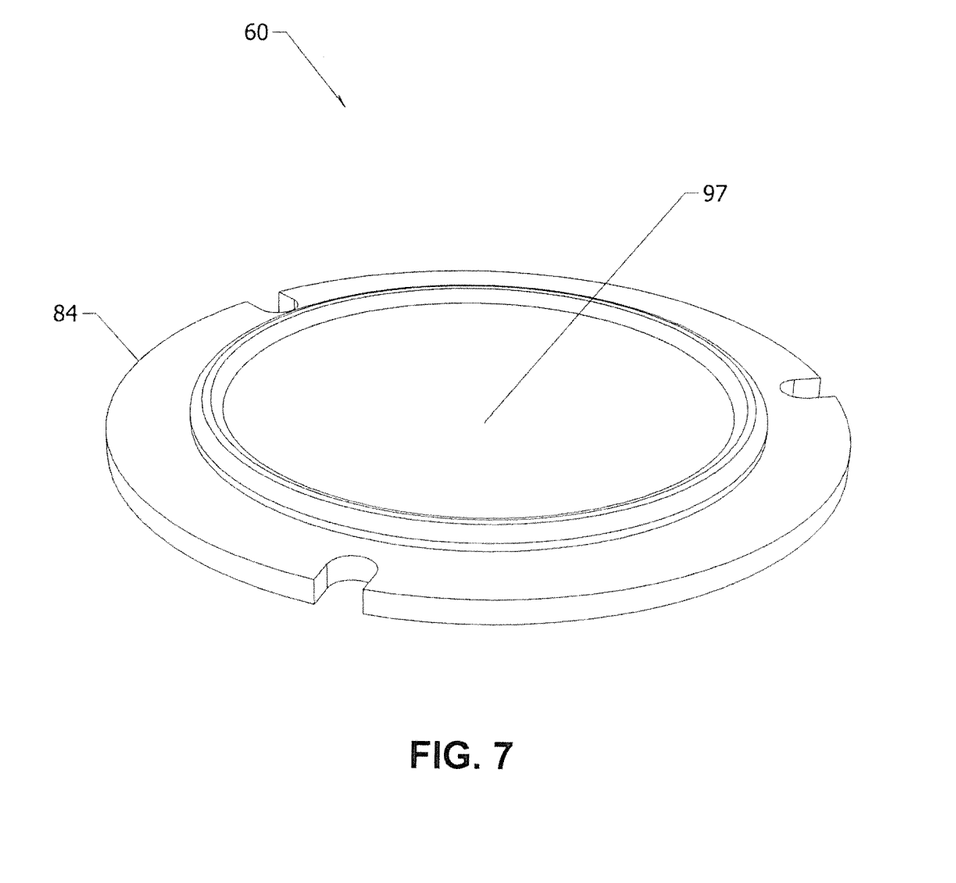
FIG. 7 is a perspective view of a platform assembly of a light emitting assembly.
Figure 8:
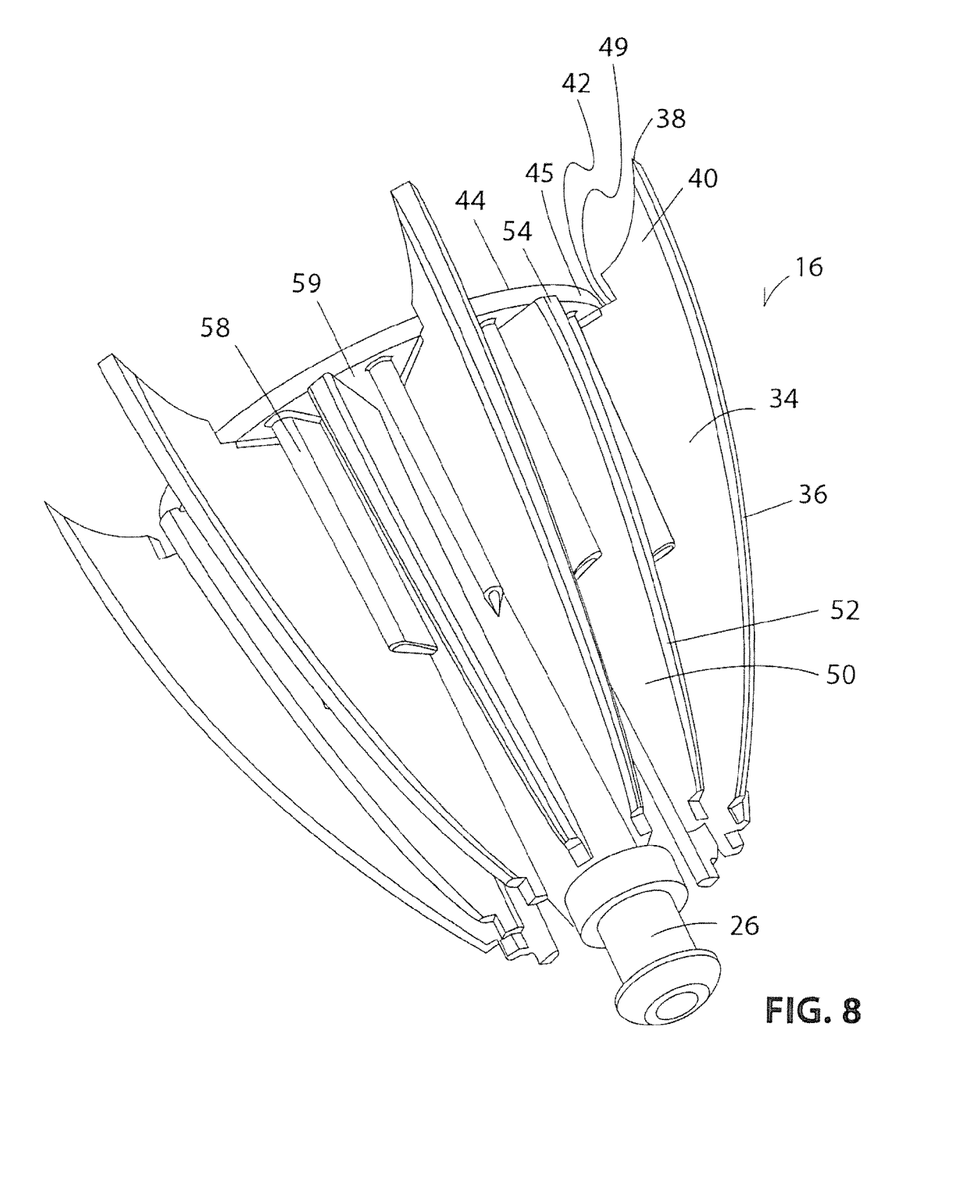
FIG. 8 is a side perspective view of a heat sink of an LED lighting assembly.

In a preferred embodiment as shown in FIG. 7 the substrate has a plurality of electrically conductive pathways or traces 86. The substrate 84 additionally functions as a heat spreader. In this embodiment the electrical component dies 64 are engaged to and run along a top surface 88 of the substrate 84 to form an interface surface 90 between each electrical component dies 64 and the substrate 84 and then have electrical connectors 92 to electrically connect the electrical component 64 to the traces 86. By engaging the top surface 88 of the substrate 84 the vectors of thermal conduction 94 are pointing across the interface surface 90 perpendicular to the interface and top surface 88 and 90.

In particular, the vectors of thermal conduction 94 are a combined and unified vector of thermal conduction. Specifically, a heat transfer vector has both magnitude and directional components such as radiation and heat dissipation or conduction. When the conduction elements of the heat transfer vector are summed together the average vector points downward and perpendicular to the plane 96 defined by the top surface 88 of the substrate 84. This summed and averaged vector is considered a combined and unified vector of thermal conduction. As a result of this combined and unified vector of thermal conduction crossing the top surface 88 perpendicular to the surface 88 efficiency of moving heat from the top surface 88 of the substrate 84 through the substrate 84 is maximized.

The combined and unified vector of thermal conduction 94, having all thermal gradients pointing/moving away from the lighting plane 96, provides a way to block other components from being able to source all the heat from the same plane (i.e., have the circuitry and LED dies being together). Therefore, in the instant design, the electrical component dies 64 have thermal vectors that point in the same direction and the thermal resistance is therefore optimized to handle the heat in this same manner.

The single vector heat direction makes it easier for the dissipation of the heat from the electrical components 64, the simplification of the entire lamp structure, to obviate the need for any cavities, to allow for decreased amount of materials to be used, and to lessen the need for moving heat to the heat sink 16. This is, in part, facilitated by the plane LED platform 60 being attached with the greatest surface area for conducting heat away from the elements (heat spreader) towards the heat sink's receiving or transfer portion of the sink 16 (the top of the sink).

The heat sink 16 may have different thermal conductive properties along the heat sink 16. That is, where the magnitude of the vector is greatest (e.g., right at the transfer point from the LED Platform and the thermal transfer receiver of the heat sink, near the attachment point of the heat sink 16 to the heat conductive substrate 84, and/or in a part of the heat sink 28 that is closest to the electrical component dies 64), the heat sink 16 may need to dissipate the greatest amount of heat. In order to diffuse more heat, the heat sink 16 may be formed such that the heat sink 16 has more material or heat fins in areas in which greater diffusion is needed.

Alternatively, the areas of the heat sink 16 responsible for more diffusion may be formed of materials with superior thermal conduction and dissipation properties. Because the heat vector is in a single direction, as the vector magnitude is reduced (some of the heat is already dissipated) in areas located further from the heat generating LED dies and circuitry, the performance of the heat sink 16 need not be as good, and the heat sink 28 may be formed with less material (e.g., a taper in the heat sink), or materials having lower thermal conduction and dissipation properties.

In another embodiment for the heat transfer, given the uniform vector, an active element for heat transfer cooling may be used. The described embodiment can include a square pipe (or other conduit for cooling agent) which has the LED Platform 60 attached or integrated along one contact point to the conduit. Within the conduit, a cooling agent, such as water, may flow to pull the heat down and/or into the conduit and the cooling agent.

In addition to moving heat more efficiently from the electrical component dies 64 through the substrate 84, this design allows the electrical component dies to lie on a single plane 96 along with the traces 86. Thus all of the electrical component dies 64 of the assembly 10 lie on the same plane 96 greatly reducing the size of the entire assembly 10 allowing for more practical functionality for the assembly 10. Further, as a result of the design, all of the heat generated by the assembly 10 lies only on the top surface 88 of the substrate 84 again increasing efficiencies, allowing for a more compact assembly 10 and providing greater ease in manufacturing the assembly 10.

A phosphor 97 is placed over the lighting platform 60 to provide a conversion material that encapsulates the LED dies 80 and other electrical component dies 64. Because the phosphor 97 or optically clear material also encapsulates the electrical component dies 64 this eliminates the need for electrical component die packaging. The phosphor 97 also converts color from blue LED dies 80 into white. All LED dies 80 in the lighting platform 60 are mounted on the single substrate 84 (e.g., on a surface of a planar substrate), and the phosphor 97 is applied over the substrate 84 (or surface of the substrate) having the LED dies 80 thereon. As such, the phosphor 97 can be easily applied to all LED dies 80 in the lighting platform 60 in a single processing step, without requiring each individual LED to have phosphor separately applied to the LED. Thus the conversion phosphor layer 97 covers a substantial portion of the substrate 84 including the electrical component dies 80, such that all of the LED dies 80 are covered by the conversion phosphor 97.

Figure 9:
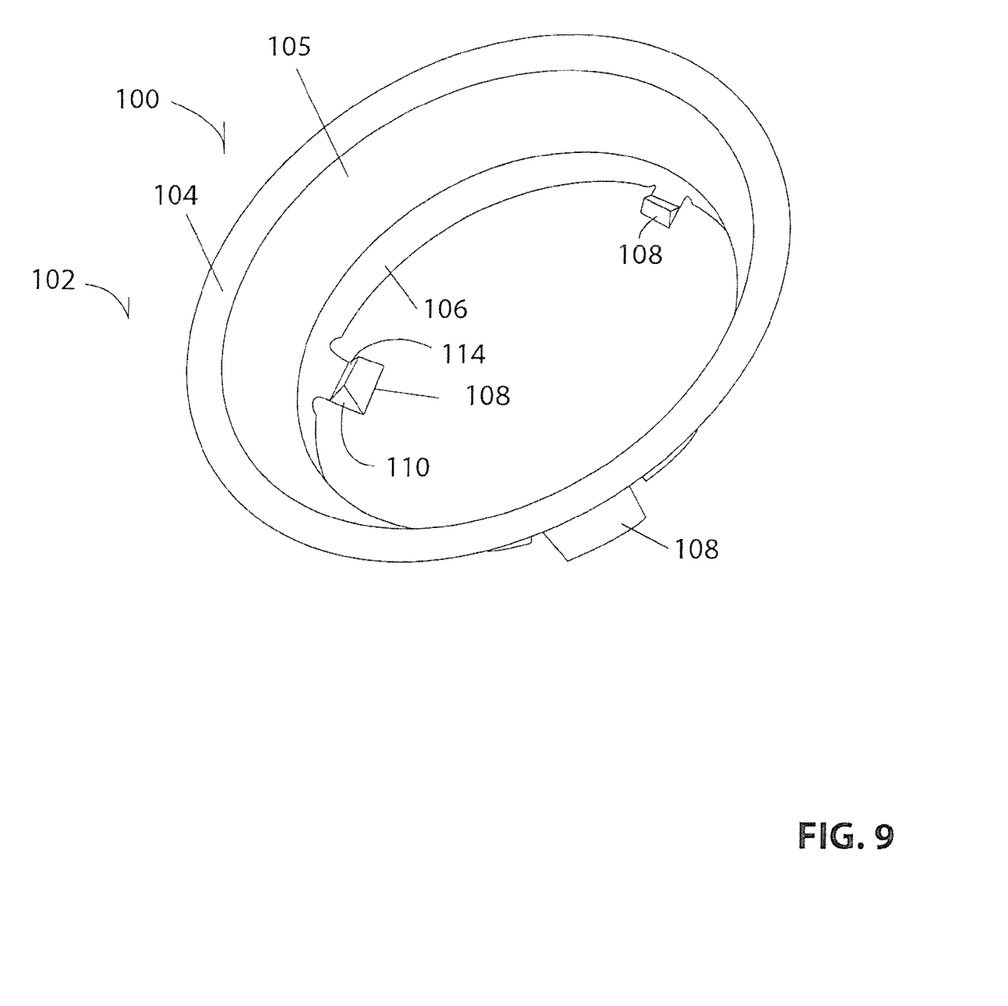
FIG. 9 is a top perspective view of a first lens section of a bulb for an LED lighting assembly.
Figure 10:
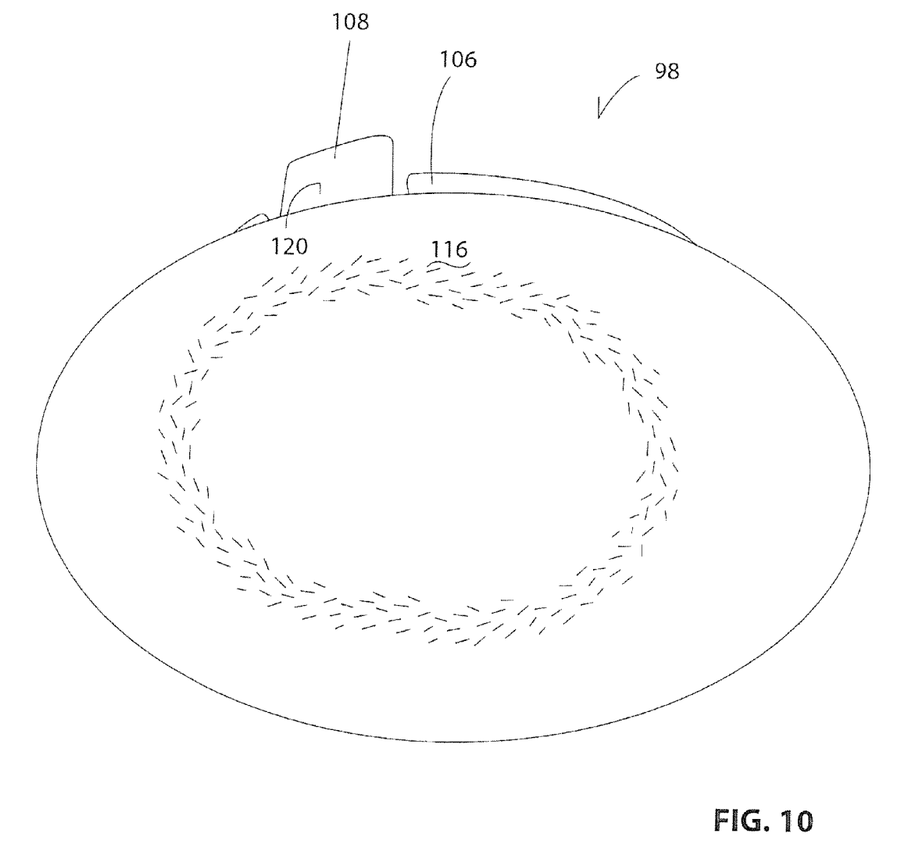
FIG. 10 is a top perspective view of a bulb of an LED lighting assembly.

FIGS. 9 and 10 shows an example of a bulb 98 that may be attached to the heat sink 16 in order to form LED lighting assemblies 10. Each bulb 98 has a first lens section 100 that has a generally frustroconically shaped first lens body 102 that has a circular top surface 104 and a continuous arcuate sidewall 105 extends downwardly and inwardly from the top surface 104 to an annular flange 106 that extends downwardly perpendicular to the top surface 104.

In one embodiment disposed in and extending past the annular flange 106 is at least one tab member 108 that is generally V-shaped and form an inclined plane element 110 that extends radially toward a central axis 112 of the first lens section 100 and terminates at a tab member flange 114. In another embodiment the first lens section 100 has three tab members 108.

The tab member 108 is thus shaped such that when the first lens section 100 is placed with the tab member 108 facing downward toward the platform base 44 onto the platform base 44 with no downward force being applied the tab member 108 rests on the platform base 44 and engages the edge 45 of the platform base 44. Once downward pressure is applied to the first lens section 100 the edge 45 of the platform base biases the tab member 108 away from the central axis 112 as the inclined plane element 110 slides along the edge 45 of the platform assembly base 44. Once the edge 45 clears the tab member flange 114 the tab member 108 snaps or is biased back toward the central axis 112 to frictionally secure the first lens section 100 to the heat sink 16. When secured the annular flange 106 of the first lens section 100 is disposed within the notch 49 adjacent the edge 45 to encapsulate the platform assembly 60.

A second lens section 116 is secured to the first lens section 100 prior to securing the first lens section 100 to the heat sink 16 such that the entire bulb is secured to the heat sink 16 in one operation. The second lens section 116 can be any size or shape as long as the bottom surface of the second lens section 116 is the same shape and size to matingly engage the top surface 104 of the first lens section 100. Along this interface the first and second lens sections 100 and 116 are secured to one another.

As a result of having a platform assembly 60 and thus LED dies 80 on a single plane on the heat sink 16 the range of lumen output is controlled by selection of materials and altering characteristics of the first and second lens sections 100 and 116 to meet different criteria to determine the lamp type of the assembly 10. In this manner identical heat sinks 16 and platform assemblies 60 can be manufactured and secured to one another regardless of the lamp type and the selection of interchangeable lens sections 100 and 116 determine the lamp type.

For example, in a first embodiment the second or top lens section 116 is made of a material that has both a high diffusion rate and high reflection coefficient. Specifically, the reflection coefficient through glass 4%, thus a reflection coefficient above 4% is considered a high reflection coefficient and a reflection coefficient below 4% is considered a low reflection coefficient. A high diffusion rate is considered any material that diffuses light more than ten degrees as compared to when the material is not used and a low diffusion rate is any material that diffuses light less than ten degrees as compared to when the material is not used.

In one embodiment this material is a white polycarbonate resin such as LUX9612™ resin made by Sabic Innovative Plastics Asia Pacific™. Meanwhile in this embodiment the bottom or first lens section 100 is made of a material having a low diffusion rate and a low coefficient of reflection. In one embodiment the material is a white polycarbonate resin such as LUX9616™ resin made by Sabic Innovative Plastics Asia Pacific™.

In this embodiment by having a top lens section 116 that has a high diffusion rate, light going through the top lens section 116 spreads out or diffuses such that an even distribution of luminous intensity within the 0° to 135° zone is achieved to meet the Luminous Intensity Distribution criteria to be considered an omnidirectional lamp. Similarly, because the top lens section 116 also has a high coefficient of reflection light is reflected toward the bottom lens section 100. Because the bottom lens section 100 has a low coefficient of reflection and low diffusion rate, the reflected light from the top lens section 116 passes through the bottom lens section 100 to maximize the total flux emitted in the 135° to 180° zone again to meet the 5% of total flux emitted in the 135° to 180° zone Luminous Intensity Distribution criteria so the assembly is considered a omnidirectional lamp. At this point only the diameter of the system needs to be varied to present the exact lamp type such as an A-19 lamp.

In a variation of this embodiment a portion of reflective material 120 is formed on the top lens section 116. In one embodiment this portion of reflective material is a metallic ring formed on the interior surface of the top lens section 116 to reflect light toward the bottom lens section 100. In another embodiment the portion of reflective material 120 is a plurality of spaced apart metallic particles formed on the interior surface again to reflect light toward the bottom lens section 100. In either embodiment, the portion of reflective material 120 functions to reflect light toward the bottom lens section 100 causing a greater amount of total flux emitted in the 135° to 180° zone in order to meet the Luminous Intensity Distribution criteria for an omnidirectional lamp type. In this manner the portion of reflective material 120 provides a boost to the omnidirectional lamp type.

In yet another embodiment the lamp type desired to be manufactured is a directional lamp such as a BR lamp type. In this embodiment the top lens section 116 selected has a low diffusion rate and low coefficient of reflection and a bottom lens section 100 having a reflective material on an interior surface. In this manner light emitted through the top lens section 116 is directed toward to a solid angle of $\pi$ sr (corresponding to a cone with angle of 120°) and any light directed toward the bottom lens section 100 is reflect toward the first lens section 100 to again keep light in the 120° angle. In this manner the assembly 10 meets the Energy Star® criteria definition of a directional lamp, that being a lamp having at least 80% light output within a solid angle of $\pi$ sr (corresponding to a cone with angle of 120°). Thus, specific lamps with specific equivalent wattages can be created in a single manufacturing process.

Figure 1:
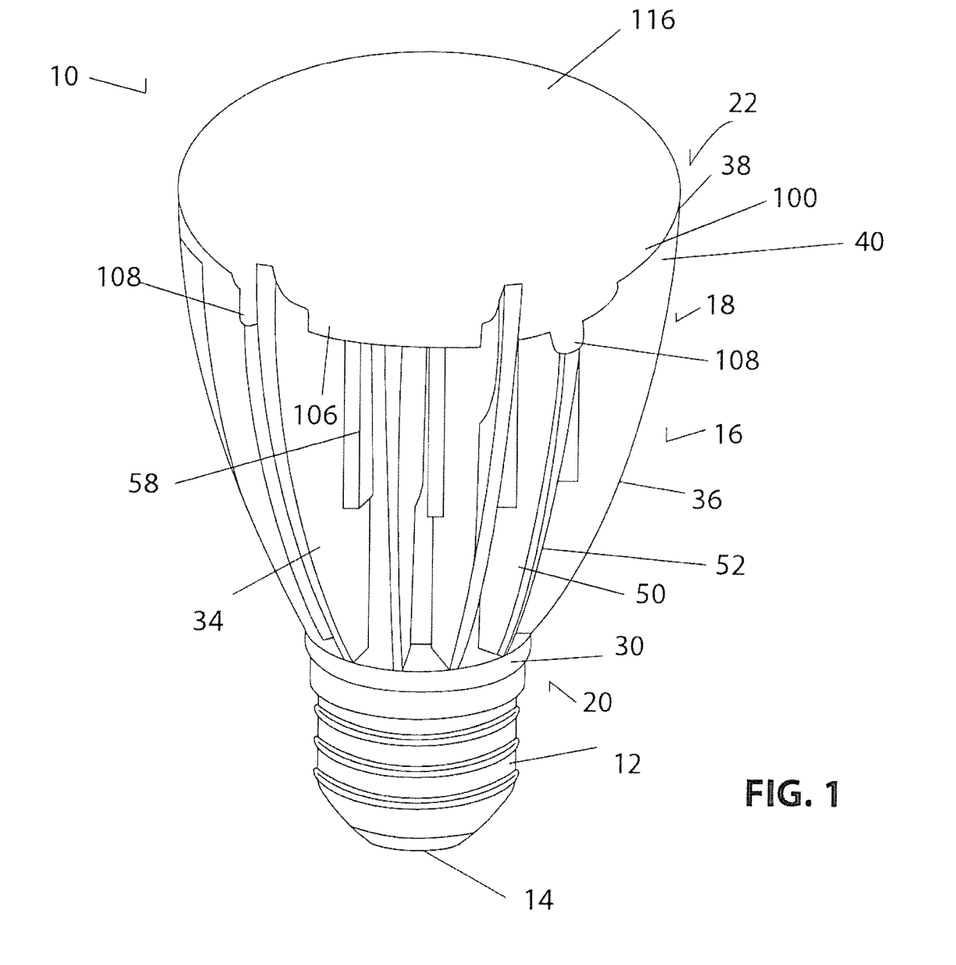
FIG. 1 is a perspective view of an LED lighting assembly without a bulb.
Figure 2:
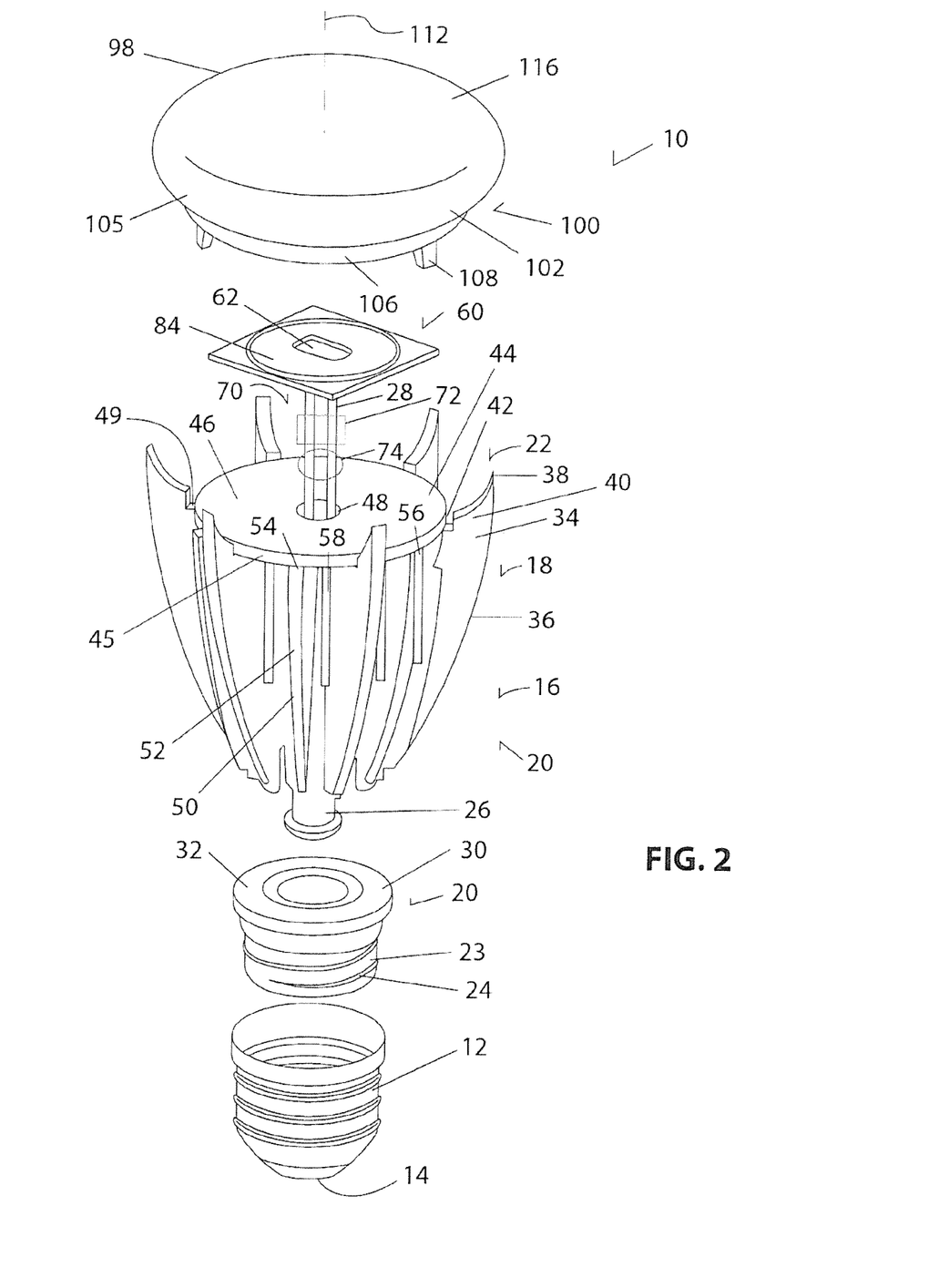
FIG. 2 is an exploded perspective view of an LED lighting assembly with a bulb.
Figure 3:
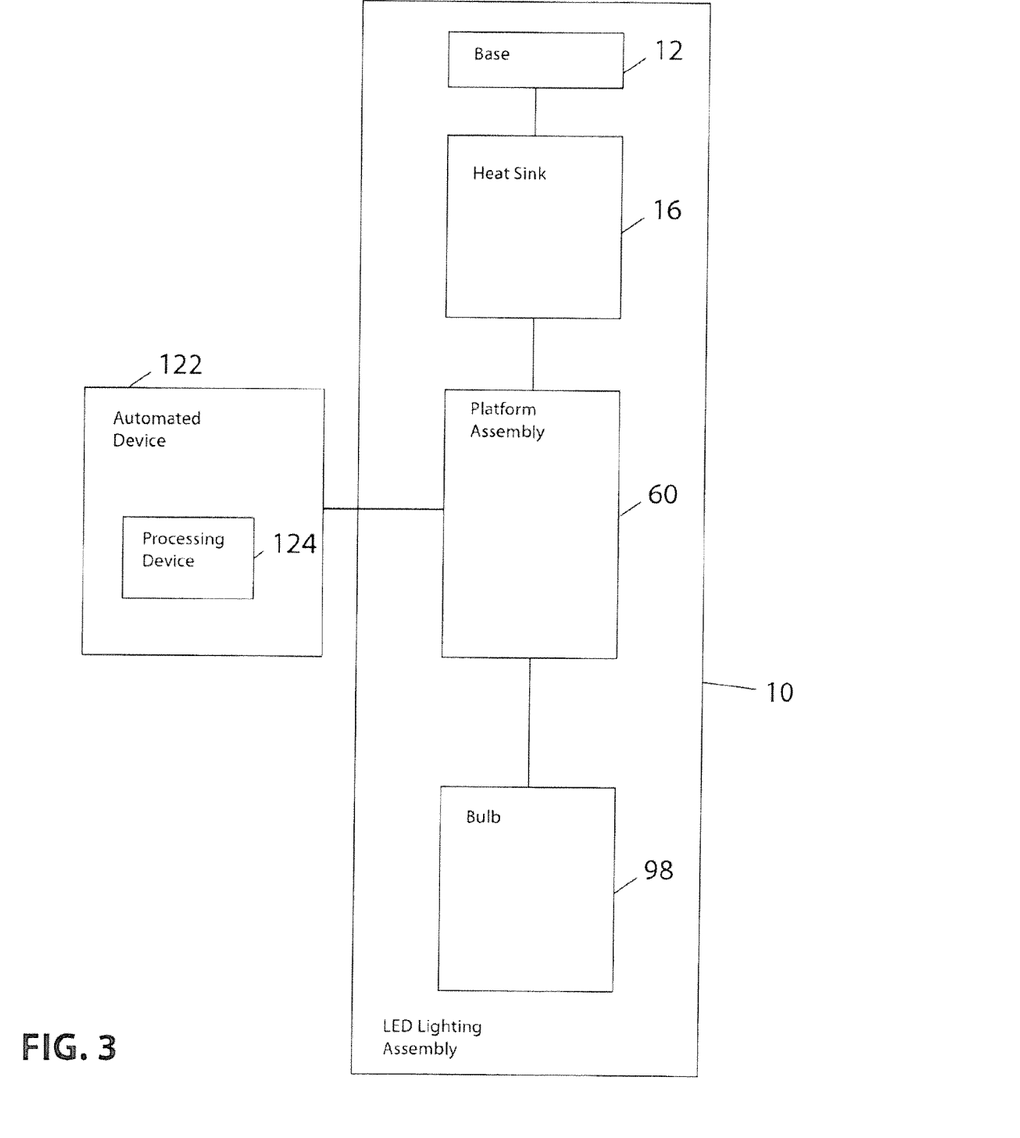
FIG. 3 is a flow diagram of a manufacturing process for an LED lighting assembly.
Figure 4:
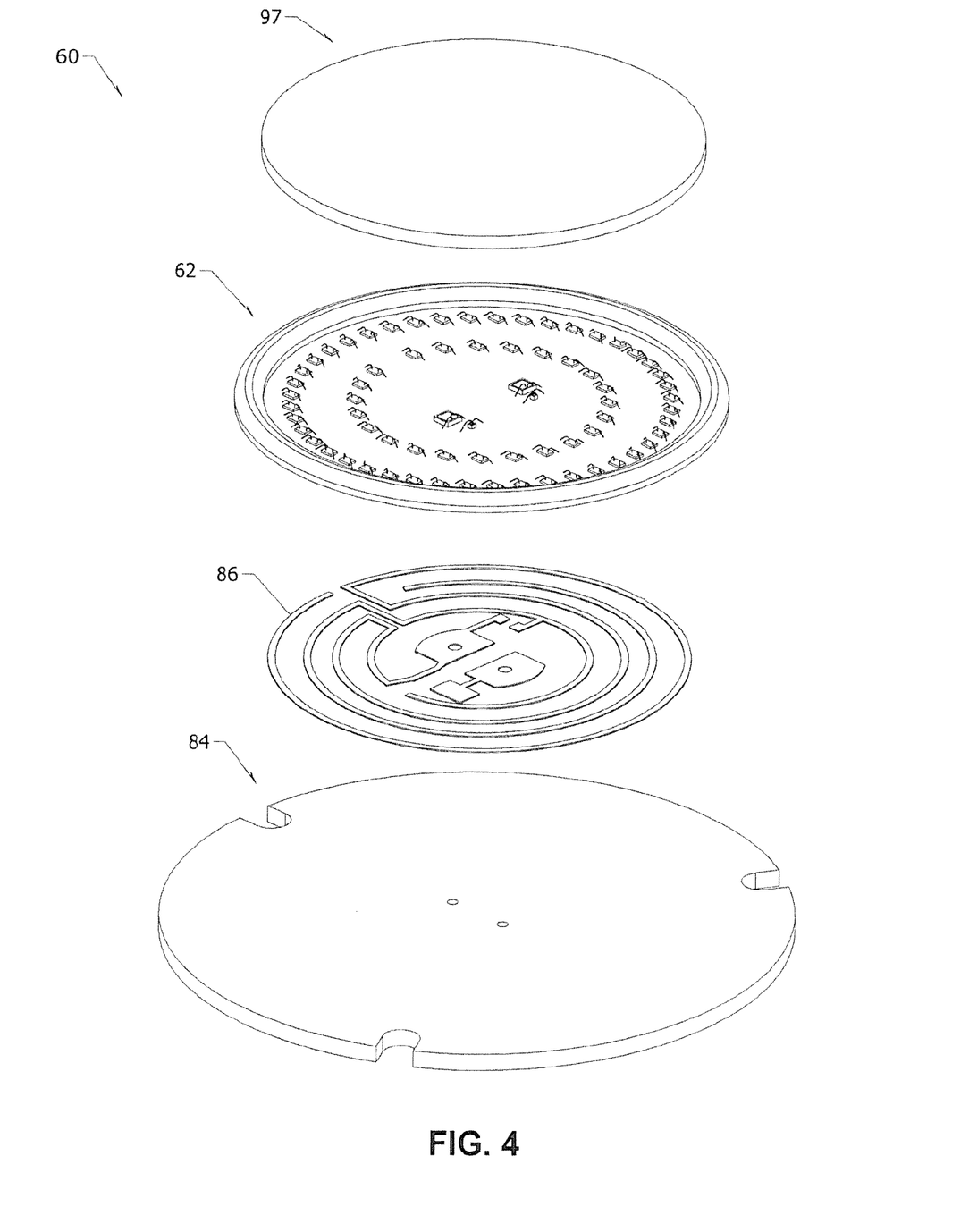
FIG. 4 is an exploded perspective view of a platform assembly of a light emitting assembly.

In operation when manufacturing the LED lighting assembly 10 a heat sink 16 is manufactured by any known manufacturing method. Similarly a base 12 is secured to the heat sink 16 and the electrically conductive elements 14 are electrically connected to the base 12 and disposed through the conduit 26 of the heat sink 16. The platform assembly 60 is manufactured using an automated device 122 that places the components 64 of the engine 62 and the electrically conductive pathways 86 on a single plane 96 of a substrate 84. Specifically the construction of the platform assembly 60 is programmed into a processing device 124 of the automated device 122. Based upon the information inputted a predetermined initial light output such as for example only 1100 lumens or a 75 Watt equivalent is determined. As a result the driving element is determined by the machine and placed on the substrate 84 so that a desired predetermined lumen output by the assembly 10. To complete the platform assembly 60 the phosphor 97 is then laid over and encapsulates the components 64 of engine 62 and the LED dies 80.

The platform assembly 60 is electrically connected to the electrically conductive elements 14 and secured to the heat sink 16, either by an electrically conductive adhesive or otherwise. Once the platform assembly 60 is secured to the heat sink 16 a bulb 98 is then connected to the heat sink 16 to surround the platform assembly 60.

The bulb 98 is formed by selecting a first lens section 100 with predetermined structure and materials and selecting a second lens section 116 based on the structure, materials and characteristics of the first lens section and securing the first and second lens sections 100 and 116 together. The bulb 98 is then frictionally secured to the heat sink 16. Based solely on the selection of first and second lens sections 100 and 116 the lamp type is determined.

Thus presented is an LED lighting assembly 10 and method of manufacturing the same. By selecting the platform assembly 60 resistance and sections 100 and 116 the Energy Star® equivalent wattage and lamp type are determined. Thus, when a new lamp type, equivalent wattage or both are required, instead of forming an entire new line to form an assembly 10 one need only switch out the type of lens sections 100 and 116 and/or change the platform assembly resistance to create the desired assembly.

As a result of the design of the improved lighting assembly 10, instead of having several different manufacturing approaches for the various components in other lights, the improved lighting platform 60 can use a common manufacturing approach for all the different components (AC circuitry, LED dies, etc.) that can be used to expedite and simplify manufacturing using the same manufacturing equipment with a silicon die and the same manufacturing techniques/technologies. Mounting of all the different components can thus be accomplished using the same technologies.

Surface mounting results in significant resistance to failure through shock, vibration or rough handling. In one instance, multiple traces (wires in the substrate) can be used (e.g., in a multi-layer substrate) so as to provide electrical connections through the substrate between two or more elements connected to the substrate. The improved LED lighting platform 60 can incorporate all the technology into the silica in die form, for example by using AC conditioning circuitry. The incorporation of the technology in die form may be made possible by having no reactive components (inductors, capacitors) or voltage shifting technologies (transformers) included in the circuitry.

Further, as a result of the platform design heat is efficiently transferred from the dies, which are thermal conducting elements to the substrate and on to the thermal interface between the substrate and heat sink. This direct rely of heat to the heat sink is vastly superior than a typical packaged LED that can include many heat resistive elements and pathways in which heat can be conveyed, including through a slug, solder, copper layer, a dielectric layer, and aluminum core and then the thermal interface to the heat sink. This is not only inefficient, but does not allow the high lumen outputs to be possible.

Consequently and improved assembly and manufacturing method are provided. Thus, at the very least all of the stated objects have been met.

What is claimed is:

1. A method of manufacturing light emitting diode lighting assemblies having different initial light outputs comprising:
    manufacturing a first heat sink using a manufacturing process;
    forming a first platform assembly having a plurality of light emitting diode lighting elements on a first substrate with an automated device;
    during the step of forming the first platform assembly, selecting with the automated device a first predetermined lumen output;
    manufacturing a second heat sink using the same manufacturing process as used to manufacture the first heat sink;
    inputting information into the automated device;
    forming a second platform assembly having a plurality of light emitting diode lighting elements on a second substrate with the automated device; and
    during the step of forming the second platform assembly, selecting a resistor with the automated device and forming the resistor onto the second substrate to provide a second predetermined lumen output based on the information inputted into the automated device.

2. The method of claim 1 wherein the first predetermined lumen output is at least 450 lumens.

3. The method of claim 2 wherein the second predetermined lumen output is at least 800 lumens.

4. The method of claim 1 wherein the first predetermined lumen output is at least 800 lumens.

5. The method of claim 4 wherein the second predetermined lumen output is at least 1100 lumens.

6. The method claim 1 wherein the first predetermined lumen output is at least 1100 lumens.

7. The method of claim 6 wherein the second predetermined lumen output is at least 1600 lumens.

* * * * *